US007126582B2

(12) United States Patent
Osborn

(10) Patent No.: US 7,126,582 B2
(45) Date of Patent: Oct. 24, 2006

(54) ABSOLUTE COORDINATE, SINGLE USER-INTERFACE ELEMENT POINTING DEVICE

(76) Inventor: John J. Osborn, 41 Salinas Ave., San Anselmo, CA (US) 94960

(*) Notice: Subject to any disclaimer, the term of this patent is extended or adjusted under 35 U.S.C. 154(b) by 329 days.

(21) Appl. No.: 10/617,596

(22) Filed: Jul. 11, 2003

(65) Prior Publication Data

US 2004/0174344 A1 Sep. 9, 2004

Related U.S. Application Data

(60) Provisional application No. 60/452,835, filed on Mar. 7, 2003.

(51) Int. Cl.
*G09G 5/08* (2006.01)

(52) U.S. Cl. .................. 345/157; 341/20

(58) Field of Classification Search ............ 345/156, 345/157, 159, 163, 173; 341/20; 178/18.01; D14/388, 389
See application file for complete search history.

(56) References Cited

U.S. PATENT DOCUMENTS 4,444,997 A * 4/1984 Danish et al. ........... 178/18.01
5,446,480 A * 8/1995 Yoshida ...................... 345/157
5,821,921 A 10/1998 Osborn et al.
6,061,004 A * 5/2000 Rosenberg ................... 341/20
6,084,571 A * 7/2000 De Gotari ................... 345/157
6,107,991 A 8/2000 Osborn
6,281,882 B1 8/2001 Gordon et al.
6,433,780 B1 8/2002 Gordon et al.
6,806,959 B1 * 10/2004 Tukker ....................... 356/484

* cited by examiner

*Primary Examiner*—Amr A. Awad
*Assistant Examiner*—Tom Sheng
(74) *Attorney, Agent, or Firm*—Dorsey & Whitney LLP

(57) ABSTRACT

A single control element device provides a user with absolute coordinate information and enables user control of a computer cursor and emulation of mouse clicks. The single control element is user-moved relative to a surface having a dynamic coefficient of friction that reduces false double-clicks. The device may be used by handicapped persons and emulates left mouse clicking and double clicking by recognizing downward force of the single control element into the surface, and recognizes upward movement of the single control element away from the surface as a right mouse click.

25 Claims, 6 Drawing Sheets

100
460
470
220
110
Z
X
420
430
230
250
450
410
190
370
Y
170
420
350
430
310
340
310
400

ABSOLUTE COORDINATE, SINGLE USER-INTERFACE ELEMENT POINTING DEVICE

PRIORITY TO CO-PENDING APPLICATION

Priority is claimed from applicant's co-pending U.S. provisional patent application Ser. No. 60/452,835 filed on 7 Mar. 2003, entitled "Absolute Coordinate, Single User-interface Element Pointing Device".

FIELD OF THE INVENTION

The invention relates generally to mouse-like pointing devices, and more particularly to pointing devices that provide the user with absolute coordinate information and a single interface element useable to move a cursor, to left click, and to right click, and to fabricating such devices with a form factor small enough to fit within a standard computer keyboard, if desired.

BACKGROUND OF THE INVENTION

Pointing devices for use with computers and other companion electronic equipment are known in the art and include trackballs, joysticks, and variations of the computer "mouse". Typically such devices require that the user move one element to control a cursor on a computer display, and then press or activate separate buttons to accomplish so-called "left-clicks" and "right-clicks". Further it is common that the user must hold such devices in a fairly rigid position during use. While such tasks may not be overly challenging for many users, these tasks can be overwhelming to handicapped users, as will now be described.

A mouse or a trackball typically has a rotatable spherical element that the user moves over a fixed surface such as a desktop to cause movement of a cursor on a computer display. However such pointing devices are not absolutely coordinate devices in the sense that the user cannot tell by looking at the device where on the computer display the cursor may be found. Conventional pointing devices include one or more user-activated buttons, for example one button to left-click (and left double-click) and perhaps a second button to right-click, where the different click functions can cause different menu options to appear on the computer screen, or a program to execute (in the case of a left double-click). A generic mouse weighs perhaps 4 oz. and is perhaps 2" wide, 5" long, and 1" in height. Commonly "left-click" and "right-click" buttons are located on the upper mouse surface, and are pressed, respectively, with the first and second fingers of the user's hand. Using the mouse to move a computer cursor on a display requires that the user move the entire mass of the mouse on the fixed surface such that the spherical element in the bottom of the mouse rotates.

More recently, the so-called optical mouse has found acceptance as a computer input device. An optical mouse often has the form factor of the older rotatable ball device. However instead of user-movement resulting in detectable rotation of a ball, an optical mouse replaces a rotatable ball with an optical emitter that directs light onto the work surface, and an optical sensor that detects light reflected by the work surface. As the user manipulates the mouse across the work surface, the optical sensor can discern relative changes in position by detecting the variation in different regions of the work surface, which variations typically are not apparent to the unaided eye. Exemplary optical mice are described in U.S. Pat. No. 6,281,882 (2001) and U.S. Pat. No. 6,433,780 (2002) to Gordon. However, manipulating an optical mouse requires essentially the same manual dexterity as manipulating a more conventional mouse, which dexterity is often not available to all would be users.

Prior art pointing mechanisms such as digitizer tablets can provide a degree of absolute coordinate information, but only while the digitizer stylus is in contact with the tablet surface. For instance if the stylus is contacting the upper right corner of the tablet, the user knows that the cursor will be in the upper right corner of the associated computer display. However as soon as the stylus is lifted from the digitizer tablet, the user can no longer look at the tablet and discern where on the computer display the cursor will be found. The stylus functions as the user-interface element to manipulate the cursor, and typically can be used to emulate left mouse-clicking.

But many users, especially physically handicapped users, find it difficult if not impossible to use prior art pointing mechanisms. Grasping and moving mice, or grasping and moving trackball devices to manipulate a cursor and then having to move a finger to click buttons may literally be impossible if the user suffers from carpal tunnel syndrome, arthritis, or perhaps has a hand prosthesis. A single user-interface element would be preferably, where the single element could be used to achieve cursor movement, and carry out the various mouse click functions. Even for non-handicapped users, the requirement of maintaining one hand on the device while pressing button(s) with a finger in a repetitive position, day-in, day-out, can result in physical disability, including tendonitis and carpal tunnel syndrome.

Some prior art pointing devices such as pressure or touchpads found on modern laptops, or the so-called Trak-Pointer™ mechanism found on IBM™ laptops can provide a dual function user-interface element that can be used for cursor movement and for left-clicking. However such devices do not provide absolute coordinate information to the user, do not provide right-clicking, and can be difficult to manoeuver, especially for the handicapped.

U.S. Pat. No. 5,821,921 (1998) and U.S. Pat. No. 6,107,991 (2000) to Osborn (applicant herein), which patents are incorporated herein by reference, disclosed pointing devices that provided the user with absolute coordinate information. The pointer mechanisms disclosed in these two patents included a user-grippable handle-like element that could better enable users, including handicapped users, to control cursor movement on a computer screen. The device described in Osborn '921 includes a peg-like element that a user could grasp to manipulate a cursor, and that could be pushed downward to emulate left mouse-clicking. The undersurface of the element would be moved by the user over a glide surface, and various resistive and/or optical mechanisms would determine the amount of movement in orthogonal x and y axes. Alternate embodiments of the '921 device included additional switches that a non-handicapped user could readily manipulate to emulate left and right mouse clicks. Among the advantages provided by devices according to the Osborn '921 and '991 patents was the substantial decrease in the magnitude of the mass of what the user was required to manipulate. For example rather than move a four ounce mouse, the portion of the device being manipulated weighed less than perhaps one ounce. Understandably for many handicapped users, and indeed for non-handicapped users, it is advantageous if computer control can be achieved while manipulating a smaller mass.

While the Osborn '921 and '991 pointing devices were absolute coordinate devices, there still was room for improvement. It turned out that double-clicking with the devices was difficult, especially for the handicapped. Excessive mechanical movement between the user-mechanism and the glide surface could occur between the movement of the first click and the second click. If the movement exceeds about three pixels on the computer display, the computer software will recognize two discrete and somewhat spaced-apart left mouse clicks, rather than a single left mouse double-click. In essence, while friction between the interface element and the underlying glide surface should be low for ease of user-controlled cursor movement, too low a coefficient of friction makes double-clicking difficult due to interface element movement between the two clicks.

What is needed is a pointing device with a single user-interface element that can be manipulated to move a cursor on a computer screen, while maintaining absolute coordinate information. Preferably the single element should be user-manipulable to emulate single and double left mouse-clicks and also a right mouse click, and should be manipulable even by handicapped users. Preferably the mass of the user-manipulated single-element should be low to reduce user fatigue. Further, the device should include a glide surface having a dynamic coefficient of friction that provides smooth rapid glide movement representing cursor movement, but that exhibits a higher coefficient of friction during mouse clicks to minimize undesired movement between mouse clicks. Preferably the device should sense the single user-interface movement using a mechanism whose form factor allows the device to be fabricated within a computer keyboard, if desired. Regardless of the device is implemented, device output to the companion computer or other equipment should of course be in an industry standard output format. Preferably such device should be implementable with a form factor sufficiently small to fit within a standard computer keyboard, if desired.

The present invention provides such a pointing device.

SUMMARY OF THE INVENTION

The present invention provides an absolute coordinate pointer device having a single control element with which even a handicapped user can manipulate a cursor on the display of a companion computer (or other electronic system). The mass of the single control element that is manipulated by the user is substantially less than the mass that must be manipulated in many prior art devices. User movement of the single control element over a glide surface is detected electronically to manipulate cursor movement. The user can press downward on the single control element once to emulate a left mouse click, twice rapidly to emulate a left mouse double-click, and can slightly lift the single element to emulate a right mouse click. The single control element can be user-changeable such that a pen-shaped element can be used for users who can grip such an element, a prosthesis-engagable element can be used for users who use a prosthesis, and so forth.

The glide surface includes a top layer that preferably exhibits a dynamic coefficient of friction such that more friction is present during slow movement such as during a double-click than during rapid movement. The top layer preferably includes a sheet of medical X-ray film or a sheet of polycarbonate material.

A pantographic embodiment enables the device to be fabricated with a form factor sufficiently small to fit within the confines of a conventional keyboard, if desired. In another embodiment, the user manipulated single control element moves a light weight surface relative to a stationary optical transmitter-sensor system. Optical mouse sensing type techniques are used to discern "mouse movement" where user-movement of the single control element moves a reflective surface relative to fixed position optical emitters and sensors. A pantographic optical sensing embodiment can be economically produced and provides a form factor sufficiently small to fit within the confines of a conventional keyboard, in addition to allowing the user to control "mouse movement" by manipulating a relatively low mass single control element.

Regardless of the implementation of the device, cursor movement data and emulated mouse-click data can be communicated to the companion computer (or other system) in conventional formats and media including, without limitation, a wired serial port, a wired parallel port, a wired USB port, a wireless coupling, including IR and/or RF energy.

Other features and advantages of the invention will appear from the following description in which the preferred embodiments have been set forth in detail, in conjunction with their accompanying drawings.

DETAILED DESCRIPTION OF THE PREFERRED EMBODIMENT

Figure 1:
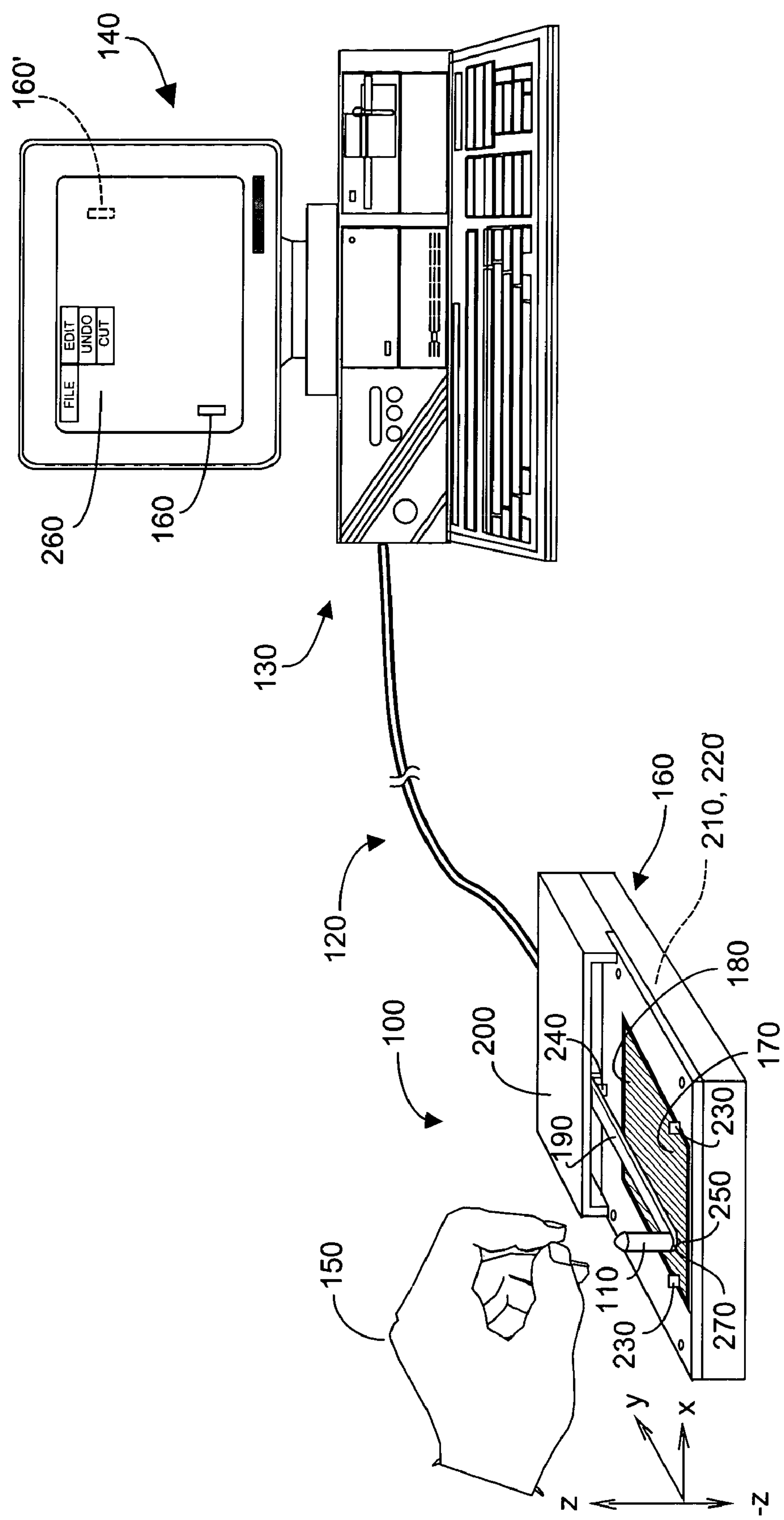
FIG. 1 depicts a first embodiment of the present invention.

FIG. 1 depicts an absolute coordinate pointer device 100 having a single control element 110 coupled via an interface 120 to a computer system 130 that includes a monitor or display 140. While interface 120 is depicted generically as a cable, it is to be understood that output signals from device 100 may instead be coupled to computer system 130 using infrared, radio signals, acoustic signals, among other communications media. Regardless of how the interface is implemented, output signals from device 100 will be received as input by computer system 130 in a format compatible with signals output from a generic off-the-shelf trackball and/or mouse input. It is further understood that while computer system 130 is shown as a PC-type computer, system 130 may in fact be a kiosk or other system to be controlled at least in part by an input device such as device 100.

As a user 150 grasps or otherwise manipulates control element 110, a cursor 160 is caused to move accordingly on display 140 as control element 110 moves across surface 170. (The user's hand 150 is shown spaced apart from control element 110 in FIG. 1 for ease of illustration.) Device 100 is termed an absolute coordinate pointer device in that a user can look at device 100 and know by the relative position between control element 110 and surface 170 where on display 140 the computer displayed cursor 160 will appear. In FIG. 1, for example, control element 110 is above the left lower corner region of surface 170, and accordingly cursor 160 is displayed at the left corner region of display 140. If user 150 manipulated control element 110 to another position on surface 170, cursor 160 would move accordingly on display 140. Thus if the control element 110 were moved to say the right corner region 180 of surface 170, display 140 would show the cursor in the right hand region, depicted as phantom cursor 160. This ability of device 100 to provide the user with absolute coordinate information is not present in conventional prior art pointing devices such as a mouse, a trackball, a joystick, or a trackpad.

Control element 110 is shown as a stub-like element in FIG. 1 that is attached to a cantilever arm 190 that projects out from the housing 200 of device 100. While arm 190 is shown as a single span, it could of course be triangular with the apex beneath control element 110, or U-shaped with the joining portion of the "U" beneath control element 110, among other configurations. The precise configuration will take into account the nature of the material comprising arm 190, e.g., plastic in the preferred embodiment, the length of the arm, the thickness of the material, and the projection length of the arm, typically about 1" or 2.5 cm. Surface 170 is sized to provide a convenient work area for the user, and is perhaps 2"×2" (2.54 cm×2.54 cm), although other dimensions could of course be used.

Within housing 200, a mechanism 210 that translates at least planar movement of control element 110 along the x and y axes of surface 170 may be resistive (as disclosed in U.S. Pat. No. 5,821,921) or more preferably optical (as disclosed in U.S. Pat. No. 6,107,991), which patents are incorporated herein by reference. Preferably, a pantographic mechanism 220 is used, coupled with an optical mechanism 210, such as disclosed in the '991 patent. Pantographic mechanism 220 is described later herein with respect to FIGS. 4A–4C, FIGS. 5A–5C, and FIG. 6.

In the '991 patent and the '921 patent, the planar surface upon which the equivalent of a control element was moved was typically made of a relatively frictionless material such as Teflon™ brand material. But often such surface was too smooth and made it difficult for a user to hold the control element in place relatively to the surface sufficiently long to complete two mouse clicks. In practice if relative movement between the control element and the surface exceeds a few display pixels, the operating system with the associated computer system will not recognize a double-click.

In the present invention surface 170 preferably exhibits a dynamic coefficient of friction. By "dynamic coefficient of friction" it is meant that surface 170 has a relatively low effective coefficient of fraction as control element 110 is user-moved relatively rapidly across the surface, but exhibits a larger effective coefficient of friction as the velocity of the movement decreases. This characteristic of surface 170 enables a user to readily move control element 110 on the surface 170, while advantageously tends to hold control element in place as user movement slows or halts, for example in preparation for a double mouse click action. Experiments by applicant have disclosed that yellow polycarbonate sheet material such as sold by Ain Plastics located in Mt. Vernon, N.Y., or exposed or unexposed medical X-ray film exhibits the desired dynamic coefficient of friction characteristics. By way of comparison, undesired relative movement between the control element and underlying surface plane in devices disclosed in the '991 and the '921 patents could be as high as about ten pixels. By contrast, in the present invention where surface 170 is polycarbonate sheet material or X-ray film material, the undesired relative movement is on the order of perhaps three pixels, which is within the acceptable range of movement for double-click recognition for Windows 98, Windows 2000 and new type operating systems.

Thus in the present invention, users, and especially handicapped users, are less plagued by problems associated with accelerated cursor movement followed by a halt and a desired double-click action. Using the described material for surface 170 allows even handicapped users to use device 100 to draw and otherwise manipulate cursor movement on an associated computer system, and to enable double-clicking action.

Typical computer type applications will call upon device 100 to enable a so-called left mouse click, a so-called right mouse click, and as noted above, a double mouse click. In FIG. 1, a spaced-apart optical transmitter-receiver 230, and/or micro-switches 240, 250 can be used to detect when control element 110 is lifted up (in the positive z-axis) or is pushed down (in the negative z-axis).

A downward push of control element 110 by user 150 in the negative z-axis deeper into surface 170 is sensed by mechanism 250 (or 230) and emulates a left mouse click. Similarly, two relatively rapid such movements are sensed by mechanism 250 (or 230) and emulate a double mouse click. When user 150 lifts control element 110 upward in the positive z-axis, away from surface 170, the movement is sensed by mechanism 240 (or other mechanism), and device 100 emulates a right mouse click.

It will be appreciated that user 150 need only manipulate the single control element 110 to draw pictures or otherwise move or control cursor 160 upon display 140, as well as to emulate left, right, and double mouse clicking. For handicapped users, the ability to control all of these functions with a single control element is highly advantageous, especially if the user does not have full use of his or her fingers. Thus even a handicapped user can select menu-type options 260 on display 140 using the single control element 110, according to the present invention.

Different users may benefit from differently shaped control elements 170.

Thus an attachment mechanism 270 preferably is used at the interface of control element 110 and arm 190 to facilitate changing the control element. If no change were desired, then mechanism 270 could be a permanent glue, or perhaps a threaded stud in control element 110 and mating threads in an opening defined in the underlying portion of arm 190. More preferably, mechanism could include a pair of strong magnets, where there is a bowl-like recess defined in the distal portion of arm 190 and a smooth mating rounded region at the lower distal end of control element 110. A strong magnet embedded in each, or perhaps a strong magnet in one and a piece of metal in the other would enable a flexible connection between element 110 and arm 190.

Figure 2:
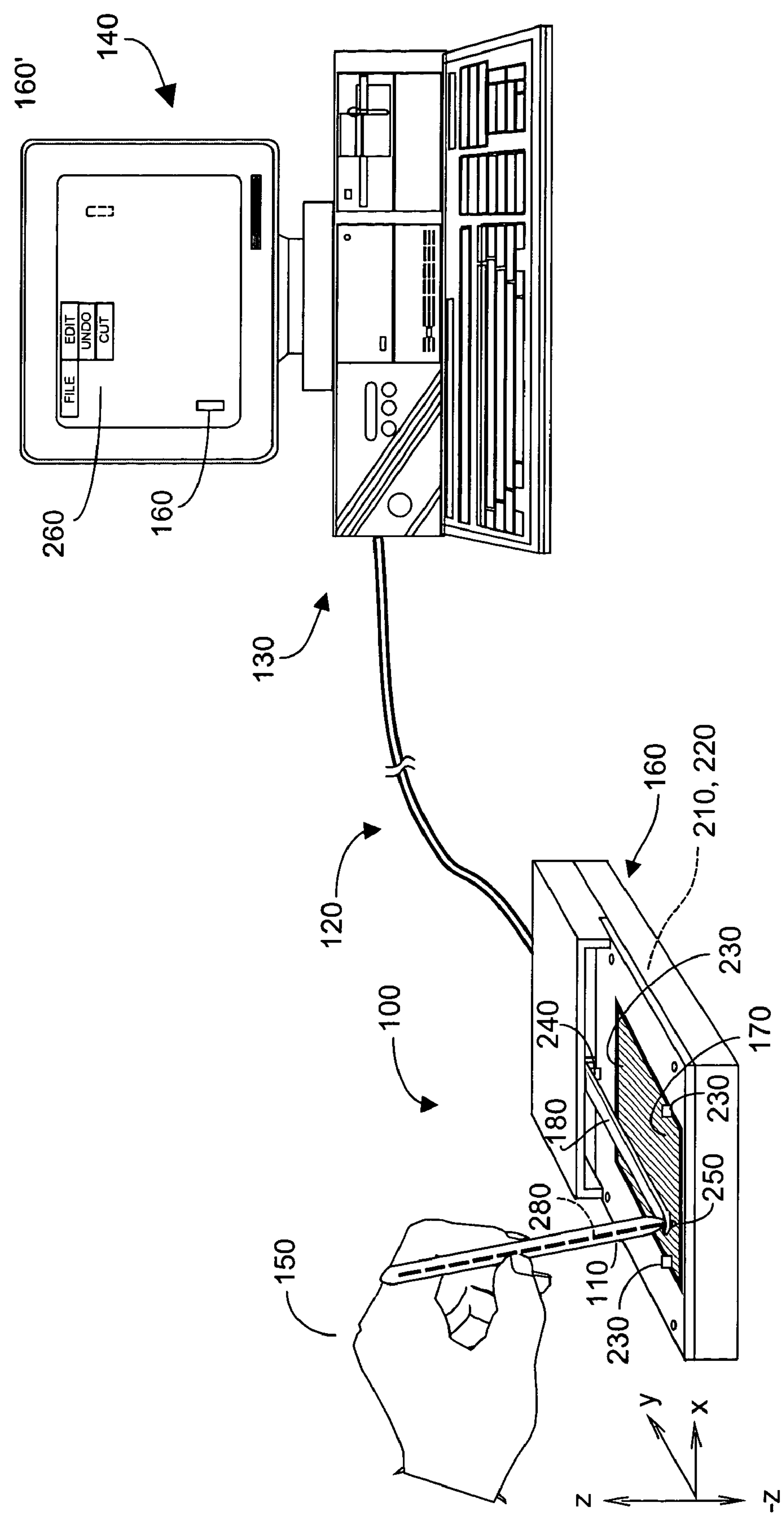
FIG. 2 depicts a second embodiment of the present invention.

FIG. 2 depicts such a flexible connection for device 100, where a longer, writing pen-like control element is now provided for a user 150 who prefers such a control element. In lieu of magnet pairs 270, a piece of elastic material 280 such as an elastic cord, could be disposed within a hollow control element 170. Cord 280 would be anchored at one end to an upper portion of the control element, and anchored at the lower end to the distal region of arm 180. Such a configuration would allow control element 110 to be moved into a position parallel to surface 170, for example when packaging device 110 for resale or shipment. Note that control element 170 could be the hollow shell of a used inexpensive ballpoint pen, with an elastic cord within. The use of such inexpensive components and construction would allow much of device 100 to be fabricated by unskilled users, perhaps even handicapped users in cottage industry type fabrication process.

Figure 3:
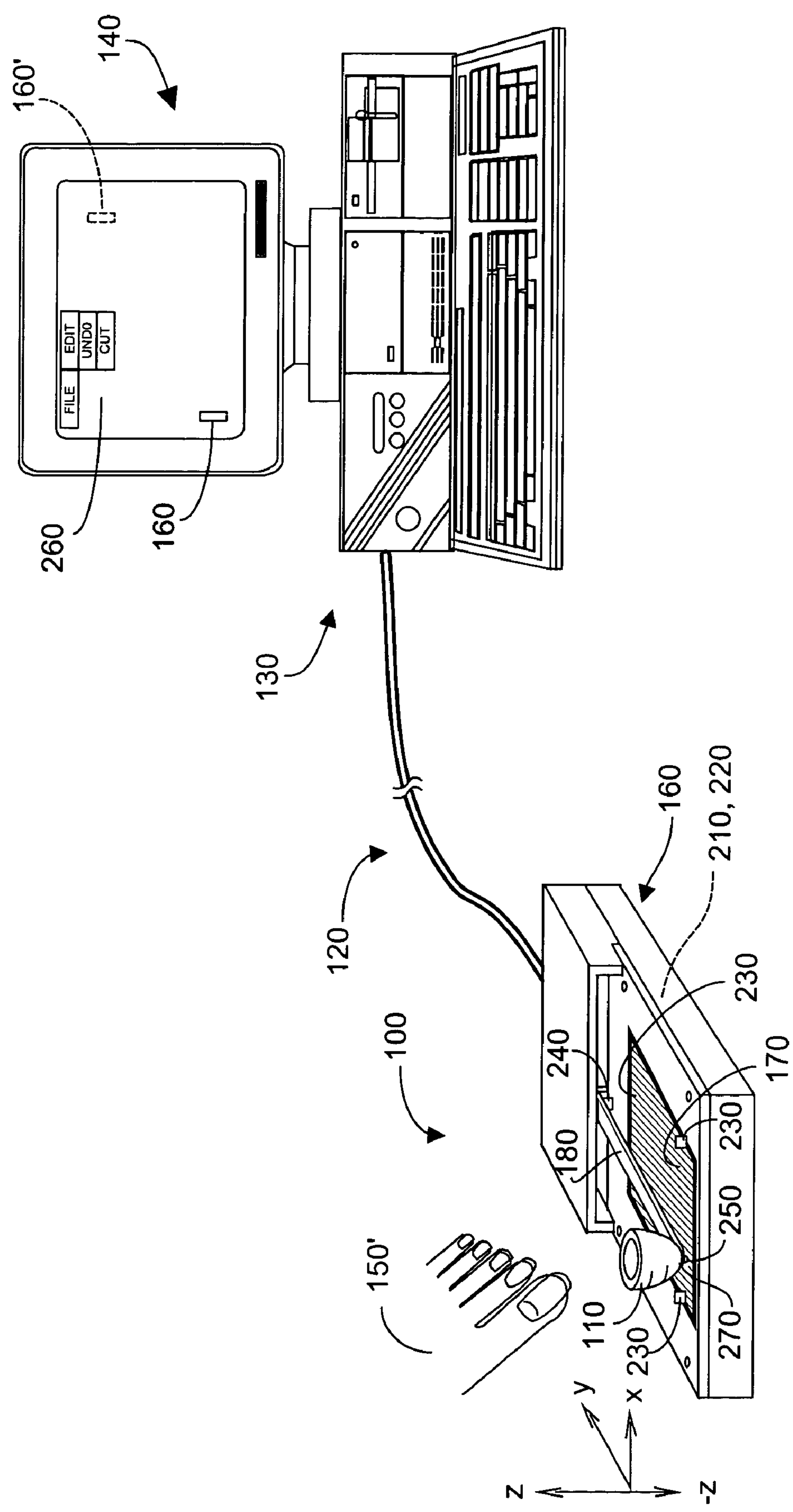
FIG. 3 depicts a third embodiment of the present invention.
Figure 4A:
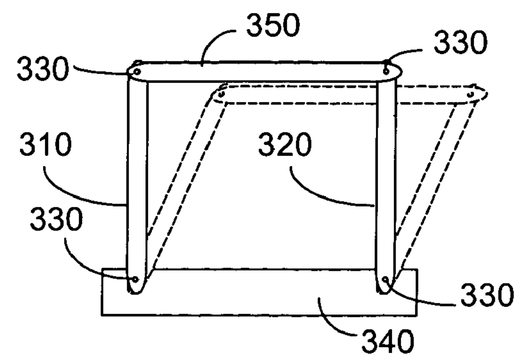
FIGS. 4A–4C are plan views of exemplary components used to provide a pantographically implemented embodiment of the present invention.
Figure 4B:
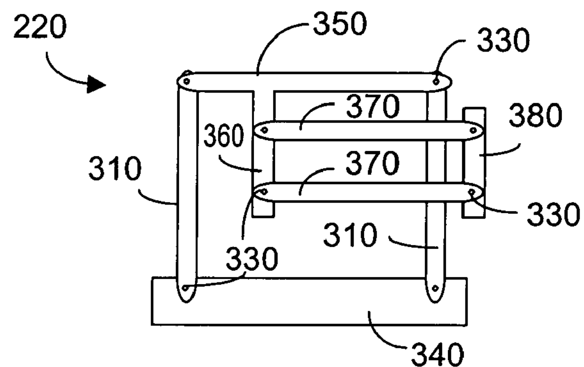
Figure 4C:
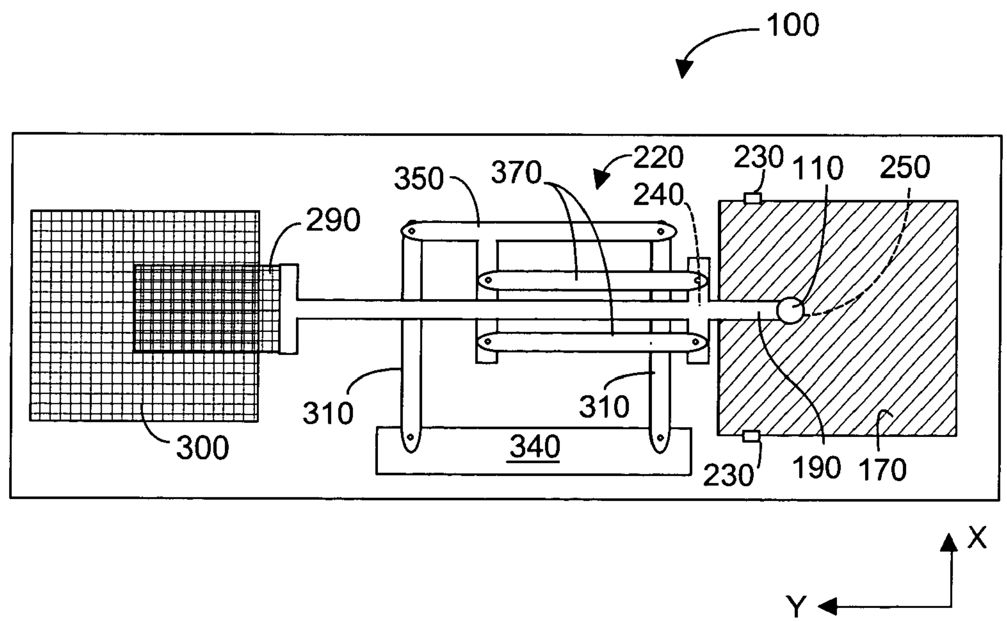

Device 100 is not restricted to individuals who enjoy the use of one or more hands. FIG. 3 shows device 100 equipped with a toe-shaped cup control element 110, which a user 150' can engage with a toe. User 150 can thus control cursor 160 on display 140, and may even be able to implement proper left, right, and double mouse clicks, depending upon user agility with toe movement. The plan views shown FIGS. 4A–4C depict components comprising a pantographic mechanism 200 for use in implementing a preferred embodiment of the present invention. Referring to FIG. 4C, mechanism 220 permits user manipulation of control element 110 at the distal end of arm 190 so as to move a film 290 relative to a stationary film 300, where each film has a grid-like pattern of parallel orthogonal lines of a desired pitch or granularity. Relative movement of film 290 will be in steps that are parallel to the x-axis and/or y-axis, with relative rotational movement being precluded. The use of such optical films was described in the '991 patent. Prior art electronics is used to sense and process light traveling through films 290 and 300, enabling enable device 100 to output mouse or trackball or trackpad type signals, recognizable by a companion computer system 130 (or other system).

In the '991 and '921 patents it was desired to constrain two components (one of which was user-manipulatable) such that movement in any direction was permitted, but rotation between the components was not permitted. Thus these earlier patents disclosed mechanical arrangements by which one of the components could move only up and down, or could only move sideways. In FIG. 4C this desired result is achieved using a pantographic mechanism 220 that permits movement of film 290, attached to the internal distal end of arm 190, relative to a fixed second film 300, without permitting relative rotation between the two films. As such, film 290 (with its grid-like pattern) can move in any direction relative to film 300 (with its grid-like pattern), except for relative rotational movement. In FIG. 4C, film 290 is intentionally drawn somewhat to the right of film 300, for ease of understanding the relationship between the two films. Those skilled in the art will appreciate that optical gain in detecting relative movement with a pantographic mechanism such as 220 can be obtained by using differently sized components in implementing the mechanism.

The evolution of pantographic mechanism 220 in FIG. 4C follows from the simpler mechanisms shown in FIGS. 4A and 4B. In FIG. 4A, spaced apart arms 310 are secured by pivot mechanism 330 at lower ends to a base member 340 and at upper ends to an upper member 350. It will be appreciated that arms 310 can be pivoted left or right, right movement shown in FIG. 4A in phantom, with the result that while upper member 350 can move, its movement is always parallel to base member 340, and never rotational.

In pantographic mechanism 220 shown in FIG. 4B, a descending portion 360 of upper member 350 is pivotally attached to the left ends of spaced apart members 370 that are pivotally joined at the opposite end to a member 380. Member 380 can be moved up and down but will always move perpendicularly to base member 340. Member 380 can also be moved left and right, but such movement will always be parallel to base member 340. Stated differently, pantographic mechanism 220 shown in FIG. 4B permits member 380 to move in two mutually orthogonal directions, but precludes rotational movement relative to base member 340.

FIG. 4C is a slight evolution of the configuration of FIG. 4B, where member 380 is now somewhat "T" shaped and functions in part as arm 190, to whose distal end is attached single control element 110. As a user moves element 110 parallel to the x-axis and/or y-axis, there results a user-controlled movement of film 290 relative to film 300 in two dimensions (e.g., parallel to the x-axis and/or y-axis, while precluding rotational movement of film 290 relative to film 300.

Pantographic mechanism 220 shown in FIG. 4C can be implemented using inexpensive, low mass, plastic components with an overall form factor that is smaller than the mechanical configurations shown in the '921 patent or the '991 patent. The associated electronics for processing light signals passed through the parallel films 290, 300 are known in the art, including for example electronic sensing as described in the '991 patent. As described earlier herein, switches 240, 250, and/or light emitters-detectors 230 are preferably included to detect user-intended mouse-clicks.

Figure 5A:
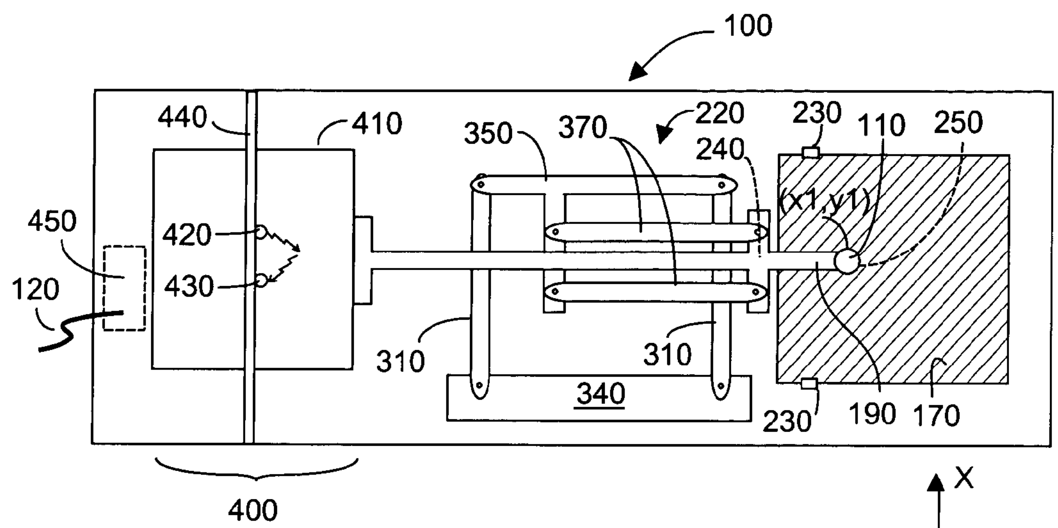
FIGS. 5A and 5B depict plan views of an exemplary optical sensing pantographically implemented embodiment of the present invention.
Figure 5B:
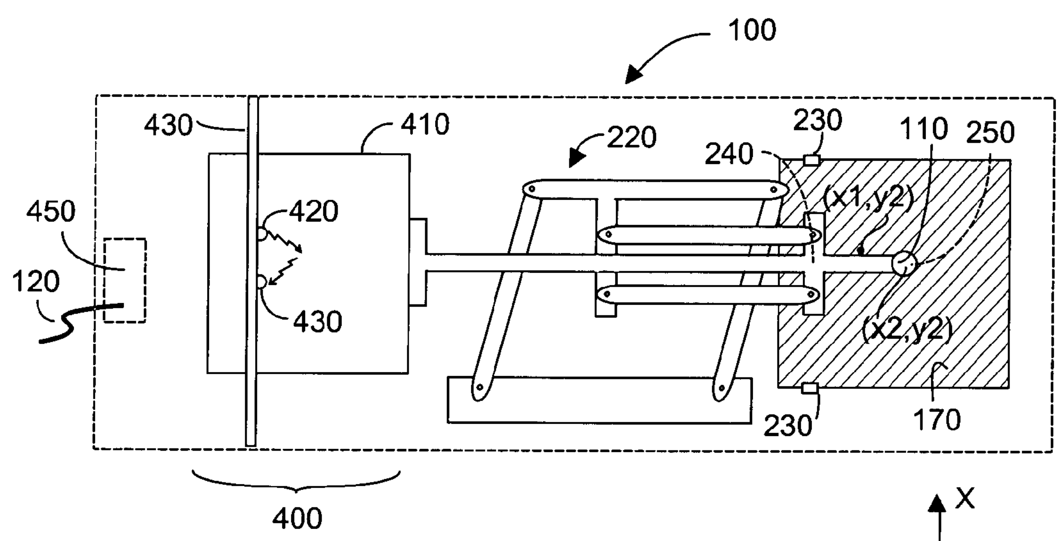

FIGS. 5A and 5B depict an embodiment of device 100 in which a pantographic or equivalent mechanism 220 is used with an optical sensing system 400 to detect user-controlled movement of single control element 110, preferably upon surface 170. In this embodiment, mechanism 220 ensures that movement of optical reflecting surface 410 is along mutually orthogonal (x,y) axis, responsive to user-manipulation of control element 110, and that no rotation of surface 410 occurs relative to the location of optical elements 420, 430 (described below). Optical elements 420, 430 are shown as being mounted on an immobile member 440 to indicate that these elements are fixed in position relative to user-movable surface 410. Optical sensing system 400 may be said to include at least one optical emitter 420, at least one optical detector 430, a reflective surface 410, which moves relative to the fixed locations of elements 420, 430. System 400 preferably also includes associated electronics 450, which discerns from reflected optical energy detection signals the movement of surface 410 proportional to movement of control element 110.

In FIGS. 5A and 5B, as the single control element 110 is manipulated by a user across or on surface 170, proportional movement of film 410 occurs relative to a fixed position optical emitter 420 and optical detector 430. Element 420 emits optical energy towards surface 410, and at least some of the energy is reflected by surface 410 to be sensed by optical detector 430. Optical emitter(s) and detector(s) 420, 420 are coupled to electronics 450, which electronics can discern different locations on surface 410 from each other as the reflective surface is, at microscopic levels, imperfect. Surface 410 may be a plane of plastic or any other preferably lightweight and inexpensive material whose reflective surface is relatively imperfect. (The topology of surfaces such as polished glass is too uniform for use as surface 410, but most other material surfaces will work.) The functioning of optical system 400, e.g., elements 420, 430, surface 410, and electronics 450, may be as described by Gordon in U.S. Pat. No. 6,281,882 (2001) and U.S. Pat. No. 6,433,780 (2002). In brief, as single control element 110 is manipulated by the user, pantographic mechanism 200 produces responsive movement of surface 410, which movement is detected by optical elements 420, 430, which are stationary.

Comparing FIGS. 5A and 5B, the control element has been manipulated to the right and slightly downward, from point (x1,y1) to point (x2,y2). As a result light emitted by emitter(s) 420 will now reflect from a different region of surface 410. The fact that surface 410 has been moved and the direction and magnitude of the movement can be detected by detector(s) 430 and electronics 450 based upon the difference in "topology" of surface 410 resulting from the (x1,y1) to (x2,y2) movement on surface 170. Electronics 450 via cable 120 (or via infra red or wireless, which may be included as part of electronics 450) communicates the movement to the associated computer system. Display 140 (see FIG. 6) would show the movement representing (x1,y1) to (x2,y2) as a cursor locus moving left to right and slightly downward. It will be appreciated that the above-described operation is somewhat analogous to an inverted optical mouse.

It is noted that in a Gordon-type optical mouse, optical emitter(s) and detector(s) within a somewhat cumbersome mouse housing are user-moved over a typically heavy and stationary reflective surface, e.g., a desktop. By contrast, in the present invention, a preferably very lightweight reflective surface (410) is moved relative to fixed optical emitter (s) and detector(s) (420, 430) in response to user-movement of a light weight, easily manipulated control element (110). Further, in a Gordon-type optical mouse, fingers are used for left and right mouse clicks, whereas in the present invention, vertical movement of the single control element is used for left and right mouse clicks. Furthermore, a Gordon-type optical mouse does not provide absolute coordinate information to the user, whereas such information is provide in the present invention by the relative position of the control element on surface 170.

Figure 5C:
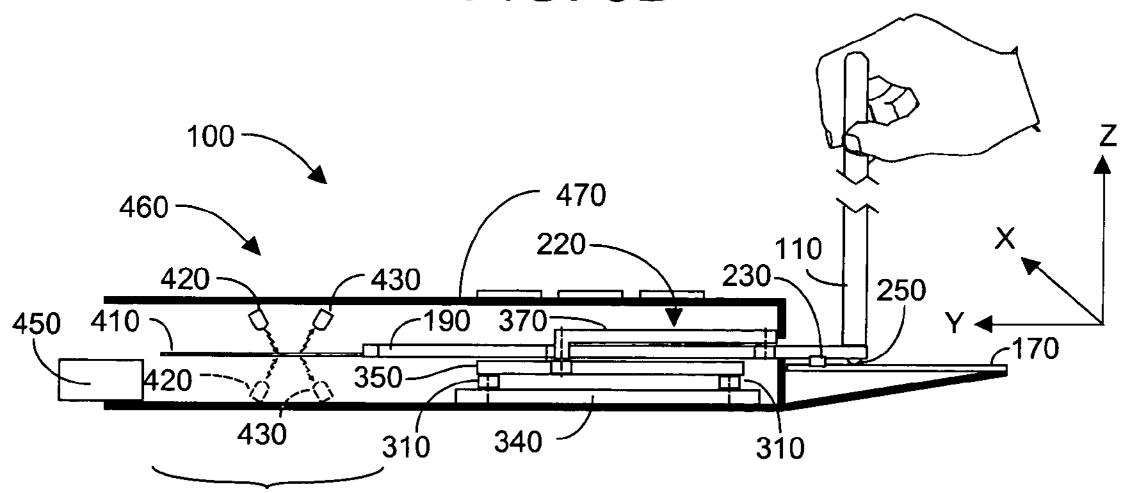
FIG. 5C is a side view of the optical sensing pantographically implemented embodiment of FIG. 5A, according to the present invention.

FIG. 5C is a cutaway side view of a keyboard 460 within whose housing 470 is disposed a pointing device 100, for example the pantographic optical sensing embodiment of FIGS. 5A–5B. As noted the form factor of pantographic mechanisms such as mechanism 220 permits fabricating pointing device 100 within a very shallow housing, for example, within housing 470 of a conventional keyboard. In the configuration shown in FIG. 5C, surface 170 protrudes from the right edge of the keyboard, although the overall dimensions of the keyboard could be increased such that surface 170 is flush with the upper surface of housing 470. Note in FIG. 5C that optical elements 420, 430 may be disposed above or below surface 410. While control element 110 is shown as being pencil-like in shape, it could instead be any other configuration suitable to the dexterity and ability of the user.

Figure 6:
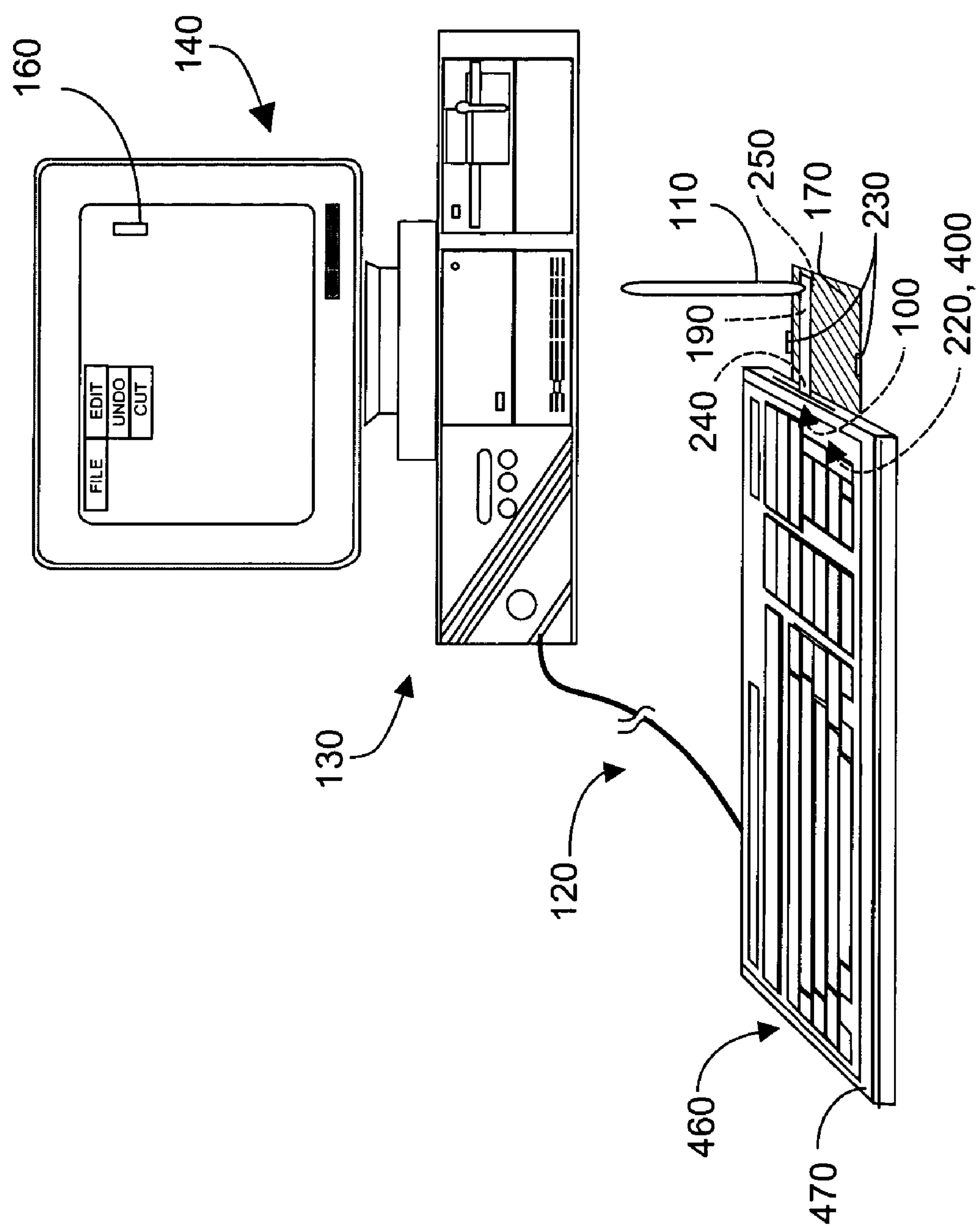
FIG. 6 depicts the embodiment of FIGS. 5A–5C of the present invention disposed within a computer keyboard.

FIG. 6 is a perspective view of keyboard 460 with device 100 as shown in FIG. 5C, fabricated within the keyboard housing. While FIG. 6 shows device 100 including pantographic mechanism 220 and optical system 400, if desired the sensing system shown in FIG. 4C could be used instead. In general, however, optical system 400 represents a good balance between low production cost and acceptable movement resolution for device 100. Implementations such as shown in FIG. 6 may be useful to keyboard manufacturers in lieu of prior art pointing mechanisms. Even if users are not handicapped, use of device 100 rather than a conventional mouse or joystick or trackball pointing device is less likely to result in carpal tunnel syndrome and fatigue. A further advantage of the pantographic optical sensing embodiment indicated in FIG. 6 is that device 100 can be mass produced in quantity for perhaps $5 unit cost.

In the various embodiment mechanical movement of control element 110 on surface 170 is detected, using resistive or more preferably optical techniques. However such user-controlled movement of element 110 could instead be detected using other mechanisms, preferably disposed beneath surface 170. Such other mechanisms could include without limitation, a pad that outputs resistance change responsive to force from control element 110, a pad that outputs capacitance changes responsive to force from control element 110, a pad responsive to pressure from control element 270, etc. If desired control element 110 could be metallic such that electrical charge from a user's body is conducted via control element 110 into a pad, disposed beneath the lower face of surface 170, which pad outputs a signal proportional to such electrical charge. If desired, surface 170 or a pad disposed beneath the lower face of a at least partially transparent surface 170, could respond to light emitted from an LED disposed adjacent to switch 250. As such, surface 170 or the pad would emit a signal responsive to location of control element 110 on surface 170. In general, however, the pantographic optical sensing embodiment of FIGS. 5A–5C, and FIG. 6 are preferred.

In summary, there any many techniques useable with the present invention to provide a signal proportional to location of control element 110 on surface 170. Regardless of the technique used, the resultant device 100 would provide absolute coordinate information and would preferably include a surface 170 exhibiting a dynamic coefficient of friction, as described herein.

Modifications and variations may be made to the disclosed embodiments without departing from the subject and spirit of the invention as defined by the following claims.

What is claimed is:

1. An absolute coordinate single control element device that enables user control of a computer cursor and emulation of mouse clicks in a computer, the device comprising:

- a single control element manipulable by a user of said device;
- a surface defining an x-y plane whereon said single control element is manipulable by said user;
- means for resolving user movement of said single control element relative to said x-y plane of said surface and for outputting a computer recognizable signal therefrom, said means including:
  - a reflective element coupled for movement along an x-axis and a y-axis of said x-y plane responsive to movement of said single control element in said x-y plane;
  - at least one stationary light transmitter disposed to direct light upon said reflective element; and
  - at least one stationary light detector disposed to detect light from said at least one stationary light transmitter reflected by said reflective element; and
  - means for recognizing user manipulation of said single control element in an axis normal to said x-y plane and for discerning therefrom at least one emulated mouse click,
  - wherein a relative position of said single control element on said x-y plane of said surface provides said user with information as to a relative position of a cursor on a computer display controlled by said device.

2. The device of claim 1, wherein said surface exhibits a dynamic coefficient of friction such that said friction between said surface and said single control element increases with decreasing rate of movement of said single control element on said surface.

3. The device of claim 1, wherein said means for recognizing discerns at least one of a left mouse click, a double mouse click, and a right mouse click.

4. The device of claim 1, wherein said means for recognizing discerns at least two of a left mouse click, a double mouse click, and a right mouse click.

5. The device of claim 1, wherein said means for resolving includes a pantographic mechanism having a first end coupled to said single control element, and having a second end coupled to said reflective element.

6. The device of claim 1, further comprising means for communicating the computer recognizable signal output from said device to said computer wirelessly.

7. The device of claim 1, wherein said single control element is manipulable by a single finger of said user.

8. The device of claim 1, wherein said single control element is manipulable by a hand of said user.

9. The device of claim 1, wherein said single control element is manipulable by a toe of said user.

10. The device of claim 1, further comprising a housing for at least a portion of said device and a computer keyboard.

11. The device of claim 1, wherein said device controls menu selection on a kiosk.

12. The device of claim 1, wherein said surface is made of X-ray film.

13. The device of claim 1, wherein said surface is made of polycarbonate material.

14. The device of claim 1, wherein said means for resolving includes a pad disposed in contact with a lower face of said surface, said pad in response to force from said single control element on said surface outputting at least one parameter selected from a group consisting of (a) resistance change, (b) capacitance change, (c) a signal responsive to magnitude of said force, (d) a signal responsive to electrical charge, and (e) a signal responsive to light from said control element detected on said surface.

15. An absolute coordinate single control element device that enables user control of a computer cursor and emulation of mouse clicks, the device comprising:

a single control element manipulable by a user of said device;

a surface defining an x-y plane whereon said single control element is manipulable by said user, said surface having a dynamic coefficient of friction such that friction between said surface and said single control element increases with decreasing rate of movement of said single control element on said surface;

a pantographic mechanism having a first end coupled to said single control element and having a second end;

a reflective element coupled to said second end of said pantographic mechanism for movement along an x-axis and a y-axis of said x-y plane responsive to movement of said single control element;

at least one stationary light transmitter disposed to direct light upon said reflective element;

at least one stationary light detector disposed to detect light from said light transmitter reflected by said reflective element;

means coupled to said at least one stationary light detector for outputting a computer recognizable signal responsive to detected movement of said single control element on said x-y plane; and means for recognizing user manipulation of said single control element in a direction normal to said x-y plane and for discerning therefrom at least one emulated mouse click, wherein a relative position of said single control element on said x-y plane of said surface provides said user with information as to a relative position of a cursor on a computer display controlled by said device.

16. The device of claim 15, wherein said means for recognizing discerns at least one of a left mouse click, a double mouse click, and a right mouse click.

17. The device of claim 15, wherein said means for recognizing discerns at least two of a left mouse click, a double mouse click, and a right mouse click.

18. The device of claim 15, further comprising:

a housing wherein is disposed said device but for said single control element; and a computer keyboard disposed within said housing.

19. The device of claim 15, wherein said single control element is manipulable by at least one of (a) a single finger of said user, (b) a hand of said user, and (c) a toe said user.

20. The device of claim 15, wherein said surface is selected from a group consisting of (a) X-ray film, and (b) polycarbonate material.

21. A method to enable user control of a computer cursor and emulation of mouse clicks using an absolute coordinate single control element, the method comprising:

providing a single control element manipulable by a user in an x-y plane to move said cursor and manipulable in an orthogonal axis normal to said x-y plane to emulate mouse clicks;

providing a surface defining said x-y plane whereon said single control element is manipulable by said user, said surface having a dynamic coefficient of friction such that friction between said surface and said single control element increases with decreasing rate of movement of said single control element on said surface;

resolving user movement of said single control element relative to said x-y plane to output a computer recognizable signal therefrom by moving a reflective element along an x-axis and a y-axis of said x-y plane responsive to movement of said single control element and by sensing movement of said reflective element using at least one stationary light transmitter to direct light upon said reflective element and using at least one stationary light detector to detect light from said at least one stationary light transmitter reflected by said reflective element, wherein movement of said single control element on said x-y plane is translated into detected movements along said x-axis and said y-axis;

detecting movement of said single control element along said orthogonal axis to discern emulated mouse clicks, and outputting a computer recognizable signal responsive to detected movements of said single control element in said x-y plane and outputting mouse click information.

22. The method of claim 21, wherein providing said single control element includes providing a single control element shaped to be manipulated by a handicapped user.

23. The method of claim 21, wherein downward movement of said single control element along said orthogonal axis emulates one of a single mouse click and a double mouse click.

24. The method of claim 21, wherein upward movement of said single control element along said orthogonal axis emulates a right mouse click.

25. The method of claim 21, wherein said surface is selected from a group consisting of (a) X-ray film, and (b) polycarbonate material.

* * * * *